United States Patent [19]

Mochida

[11] Patent Number: 4,797,258
[45] Date of Patent: Jan. 10, 1989

[54] CHEMICAL REACTION APPARATUS
[75] Inventor: Ei Mochida, Tokyo, Japan
[73] Assignee: Mochida Pharmaceutical Co., Ltd., Tokyo, Japan
[21] Appl. No.: 794,551
[22] Filed: Nov. 4, 1985
[30] Foreign Application Priority Data Nov. 10, 1984 [JP]  Japan ................. 59-236907

[51] Int. Cl.$^4$ ............................................. G01N 35/04
[52] U.S. Cl. ..................... 422/65; 198/411; 198/415; 436/47
[58] Field of Search ............... 422/65, 66, 63; 901/7; 436/44, 47, 48, 808, 890; 435/291; 366/218; 198/415, 411; 141/171, 164

[56] References Cited

U.S. PATENT DOCUMENTS

| 914,188 | 3/1909 | Robinson | 366/218 |
| 3,645,690 | 2/1972 | Rochte et al. | 436/48 |
| 4,373,431 | 2/1983 | Wallick et al. | 198/415 |
| 4,479,720 | 10/1984 | Mochida et al. | |
| 4,482,636 | 11/1984 | Mochida et al. | |
| 4,609,017 | 9/1986 | Coulter et al. | 422/100 |

FOREIGN PATENT DOCUMENTS

| 1155052 | 9/1963 | Fed. Rep. of Germany | 141/171 |
| 2055138 | 5/1972 | Fed. Rep. of Germany | 141/171 |
| 58-36631 | 3/1983 | Japan | |
| 58-61469 | 12/1983 | Japan | |

Primary Examiner—Michael S. Marcus
Attorney, Agent, or Firm—Parkhurst, Oliff & Berridge

[57] ABSTRACT

A chemical reaction apparatus is disclosed which comprises endless travelling belt(s) disposed to support in place a multiplicity of juxtaposed reaction containers having the axes thereof falling in a plane inclined from the horizontal plane and adapted to travel in a substantially horizontal direction perpendicular to the axes of the reaction containers; endless retaining belts disposed adjacent and not contiguously to the aforementioned travelling belts and provided with a multiplicity of teeth projecting up as at fixed regularly spaced intervals slightly greater than the diameters of the reaction containers so as to enable the reaction containers accommodated in the intervening spaces between the teeth to be held in fixed positions in an arrayed pattern; a base adapted to support in place the bottoms of the aforementioned reaction containers rotated about the axes thereof in an inclined state by the aforementioned travelling belts and the aforementioned retaining belts; and a drive mechanism for intermittently driving the aforementioned retaining belts and thereby effecting pitched movement of the aforementioned reaction containers.

64 Claims, 5 Drawing Sheets

Fig.4(I) Fig.4(II)
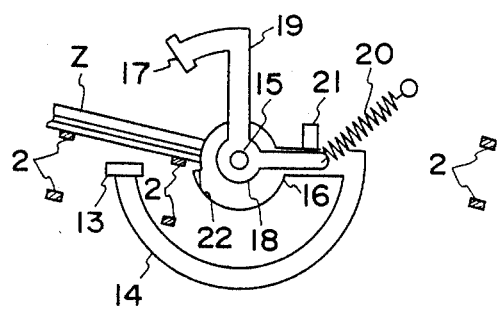
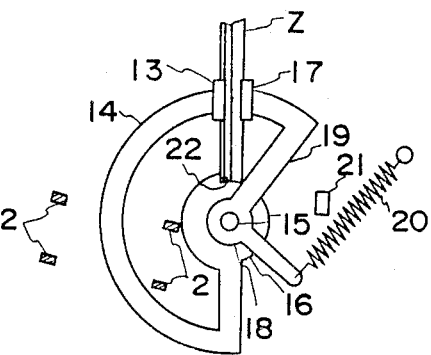
Fig.4(III) Fig.4(IV)
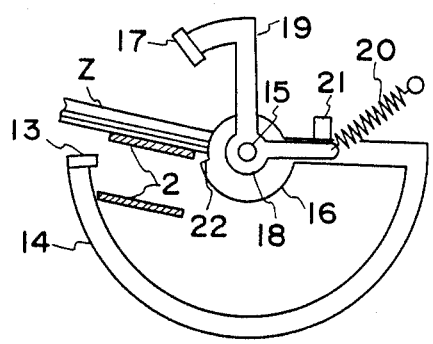
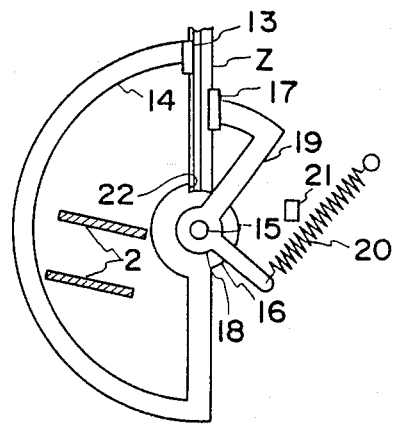
Fig.4(V)
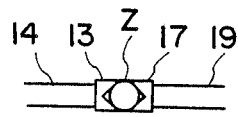

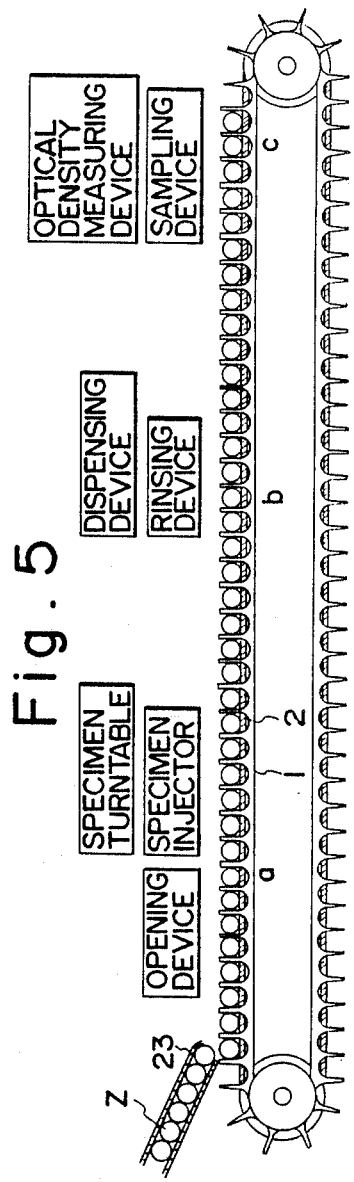

CHEMICAL REACTION APPARATUS

BACKGROUND OF THE INVENTION

This invention relates to a novel reaction apparatus for enabling a chemical reaction to be carried out simply and efficiently, and more particularly to an apparatus most suitable for automatically processing various steps of a chemical reaction. For example, this apparatus is not only usable in a wide range of chemical industries including biochemistry but also adaptable for efficiently processing various tests in biochemical and microbiochemical studies and in clinical diagnosis.

Chemical reactions are classified under a large number of types. Generally in any chemical reaction, the conditions such as temperature, pressure, time, light, and stirring under which the reaction is carried out have very large effects upon the results of the reaction. Among these factors, stirring has an conspicuous effect on the chemical reaction involved. Chemical reaction apparatuses are provided, therefore, with various stirring means adapted specifically to suit their purposes. For a large chemical reaction apparatus, a stirring device normally in the form of a propeller is set inside a tank. Then, optimal reaction conditions are established theoretically and empirically by the selection of the shape of the propeller, the variation of the rotation speed of the propeller, etc. The incorporation of such a stirring device as a propeller, however, becomes increasingly difficult as the reaction container diminishes in size. In the culture of a microorganism, the operation of stirring is simplified by collectively shaking the reaction containers.

The conventional stirring method described in the preceding paragraph, however, has a disadvantage such that the uniformity of stirring decreases in proportion as the reaction containers diminish in size.

In recent years, the practice of diagnosing various diseases by using various chemical reactions, particularly immunochemical reactions, has been finding growing acceptance. The specimen for this diagnosis is mainly the blood of a given patient. Since this amount of blood is limited and must be used for various tests, the amount of blood available for each test would become quite small. Consequently, the reaction containers used for individual test items are liable to come in smaller sizes. Since no effective means of stirring had been proposed for use in such small chemical reaction containers, it was inevitably necessary to let the reaction containers stand without any stirring until the reactions initiated therein proceeded amply. Thus there had been a disadvantage such that the total reaction time took several hours to several days.

Despite this disadvantage, immunochemical reaction using a radioisotope or an enzyme is frequently resorted to in the diagnosis of cancer and many other diseases. This is because this reaction decisively excels over other methods of diagnosis in both sensitivity and reliability. The presence or absence of a disease and the condition of the disease are determined by accurate measurement of the contents of substances in the blood which serve as criteria for diagnosis. Thus, increasing significance has come to be placed on the accuracy and the reliability of the measurement in recent years.

At present for such diagnosis the use of immobilized antibodies is widely accepted. As the solid phase for immobilizing antibody, finely divided particles or beads made of plastic or glass are used. At times, the lower part of the inner surface of the reaction container may be utilized as the solid phase. Generally in a chemical reaction, the components which take part in the reaction are dissolved in a homogeneous solution and are allowed to move freely therein. The chemical reaction is accelerated when the solution is stirred or otherwise agitated so that the components therein will be given a better chance of mutual collision. If any of the components taking part in the chemical reaction is immobilized onto a solid surface, the mutual collision of the components is greatly restrained and consequently the speed of the chemical reaction notably decreases. In such a case, stirring is used as a means of promoting the progress of the reaction. A solution, however, has not yet been found to overcome the aforementioned disadvantages which occur particularly when using a multiplicity of reaction containers each of a small volume.

The instant inventors and his colleagues continued the search for a solution to the problems encountered by the conventional technique as described in the preceding paragraph. They have consequently found that particularly in the case of small reaction containers where a stirring apparatus such as a propeller cannot be inserted, the inclined rotation of the containers themselves brings about faster reaction and highly accurate results.

The present invention has been accomplished on the basis of this knowledge of the inventors. The instant inventor and his colleagues have already devised several inclined rotation apparatuses. One of the apparatuses (type A) comprises a multiplicity ("n" in number) of rollers possessed of a fixed diameter approximating the diameter of cylindrical reaction containers and juxtaposed in parallel and inclined at a fixed angle, so that the reaction containers (a total of "n−1" in number) placed one each on every two adjacent rollers will be rotated by the rotation of the rollers in one direction at a fixed speed (Japanese patent application Laid-open No. SHO 58(1983)-36631, U.S. Pat. No. 4,482,636). Another of the apparatuses (type B) comprises two parallel chains each provided thereon with a multiplicity of freely rotatable equally spaced rollers such that every two adjacent rollers on one of the two chains will support the reaction containers near the mouth and every two adjacent rollers at the corresponding position on the other chain will support them near the bottom, and as a result, the multiplicity of reaction containers will be held in an inclined position in much the same manner as attained by the rollers of the apparatus of type A described above (Japanese patent application Laid-open No. SHO 58(1983)-36631, U.S. Pat. No. 4,482,636). This apparatus is enabled to impart a desired rotation to the reaction containers by moving in one direction an endless belt adapted to hold down the reaction containers. It is otherwise enabled to effect intermittent delivery of the reaction containers by causing the chains to be driven at fixed intervals of time, whereby each reaction container will stop at the exact position of the preceding container. Yet another of the apparatuses (type C) comprises a multiplicity of cylinders inclined and rotated as inclined at a fixed speed so that the reaction containers inserted one each in the interior of the cylinders will be automatically rotated (Japanese patent application Laid-open No. SHO(1983)-61469, U.S. Pat. No. 4,479,720). Generally, in the performance of a chemical reaction, there must be interposed various steps such as, for example, fractionation, addition of specimen and reagents, washing of reaction containers, and sampling of reaction mixtures for the determination of the degree of progress of reaction. Of the apparatuses described above, that of type A is simple mechanism where the rotation speed can be highly controlled, but it has a disadvantage of hampering incorporation therein of a device permitting further improvement of the mechanism to the semi-automatic or full-automatic level. On the other hand, the apparatus of type B is capable of advancing the reaction containers intermittently at a fixed pitch. Since this apparatus has the reaction containers held down by the belt draped thereon, however, it does not permit ready incorporation therein of a manual or automatic hopper unit capable of supplying reaction containers at the outset of the operation of the apparatus or a unit for release of reaction containers. It also entails the disadvantage that it permits no easy incorporation therein of a mechanism which enables a reaction container located at a desired position to be raised to an upright posture and, therefore, proves inconvenient for the automation of such steps as rinsing the interior of the container and replacement of reaction mixture. The apparatus of type C is convenient for solely manual operation similar to the apparatus of type A. When it is desired to adapt this apparatus so as to permit the aforementioned intermittent advancement of reaction containers similar to type B, the adaptation inevitably entails complication of the mechanism as by the incorporation of a turntable system wherein a plurality of cylindrical holders are equally spaced in a circumference having as its center the central axis perpendicularly intersecting an inclined disk and further wherein each cylindrical holder is adapted to be rotated about its respective axis perpendicularly intersecting the inclined disk, so that the reaction containers in the cylindrical holders will be intermittently advanced by a fixed pitch each time the inclined disk is rotated by one pitch over a fixed time. In the adapted apparatus, when a given step is desired to be carried out with the reaction container held upright, this apparatus necessitates further incorporation of a complicated mechanism because the reaction container cannot be held upright unless it is removed from the cylindrical holder.

SUMMARY OF THE INVENTION

An object of this invention is to provide a chemical reaction apparatus which is mechanically simpler than any of the conventional apparatuses of the class and which permits a given chemical reaction to be continuously performed automatically on a multiplicity of dissimilar samples by combining devices necessary for various steps of the process involved such as addition of specimens, rinsing the inside of the reaction containers, and sampling of reaction mixtures, and interlocking these devices in accordance with a preset program.

The chemical reaction apparatus of this invention is constructed as follows. To be specific, this invention is directed to a chemical reaction apparatus which is characterized and comprised of at least one endless travelling belt supporting thereon a multiplicity of cylindrical reaction containers arranged in parallel and being advanced continously by drive means at an equal speed in one horizontal direction perpendicular to the central axes of said containers, separate endless retaining belts disposed in parallel and not contiguously to said travelling belt, provided thereon with a multiplicity of teeth projecting up at fixed, spaced intervals slightly greater than the diameter of the reaction containers, and adapted to retain the said reaction containers at fixed relative positions, a base for supporting the bottoms of the said reaction containers, and drive means for advancing the retaining belts intermittently over fixed intervals of space, whereby the multiplicity of cylindrical reaction containers of same size are juxtaposed with their mouths up and their axes falling in a plane inclined at a fixed angle from the horizontal plane, rotated about their own central axes at a fixed rotational speed while retained in the positions at the angle of inclination both mentioned above so as to allow a required chemical reaction to proceed within and to be supported in place by the base. This invention is further directed to a chemical reaction apparatus which is provided with injection means for introducing reagents into the aforementioned reaction containers in an inclined state, rinsing means for evacuating the aforementioned reaction containers in the inclined state of spent reaction mixtures and then rinsing the interiors of emptied reaction containers, opening means for removing seals from the reaction containers in the inclined state when the reaction containers are kept tightly sealed, sampling means for drawing samples of reaction mixtures from the aforementioned reaction containers in the inclined state, measuring means for testing the reaction mixtures in the reaction containers for optical density, and reading means for optically or electromagnetically reading the input data displayed in advance on the outer surfaces of the aforementioned reaction containers in the inclined state.

This invention is further directed to a chemical reaction apparatus which is characterized by being provided at least at one location with raising means for setting upright the aforementioned reaction containers as supported at the bottom thereof or picked up from above. It is also directed to a chemical reaction apparatus which is provided with injection means for introducing reagents into the aforementioned reaction containers in the upright state, rinsing means for evacuating the aforementioned reaction containers in the upright state of the spent reaction mixtures and then rinsing the interiors of emptied reaction containers, opening means for removing seals from the aforementioned reaction containers in the upright state when the reaction containers are kept tightly sealed, sampling means for drawing samples of reaction mixtures from the aforementioned reaction containers in the upright state, measuring means for testing the reaction mixtures in the aforementioned reaction containers in the upright state for optical density, and reading means for optically or electromagnetically reading the input data displayed in advance on the outer surfaces of the aforementioned reaction containers in the upright state.

BRIEF DESCRIPTION OF THE DRAWINGS

FIG. 4 illustrates a raising mechanism for setting upright a reaction container.

FIG. 4(I) is a diagram illustrating the raising mechanism in the standby state in an apparatus using two travelling belts.

FIG. 4(II) is a diagram illustrating the raising mechanism already operated to set upright the reaction container in FIG. 4(I).

FIG. 4(III) is a diagram illustrating the raising mechanism in the standby state in an apparatus using one travelling belt.

FIG. 4(IV) is a diagram illustrating the raising mechanism already operated to set upright the reaction container in FIG. 4(III).

FIG. 4(V) is a top view illustrating the reaction container set upright by the raising mechanism.

FIG. 5 is a front view of the configuration of the apparatus corresponding to the process of the immuno-reaction.

DETAILED DESCRIPTION OF THE PREFERRED EMBODIMENT

Figure 1:
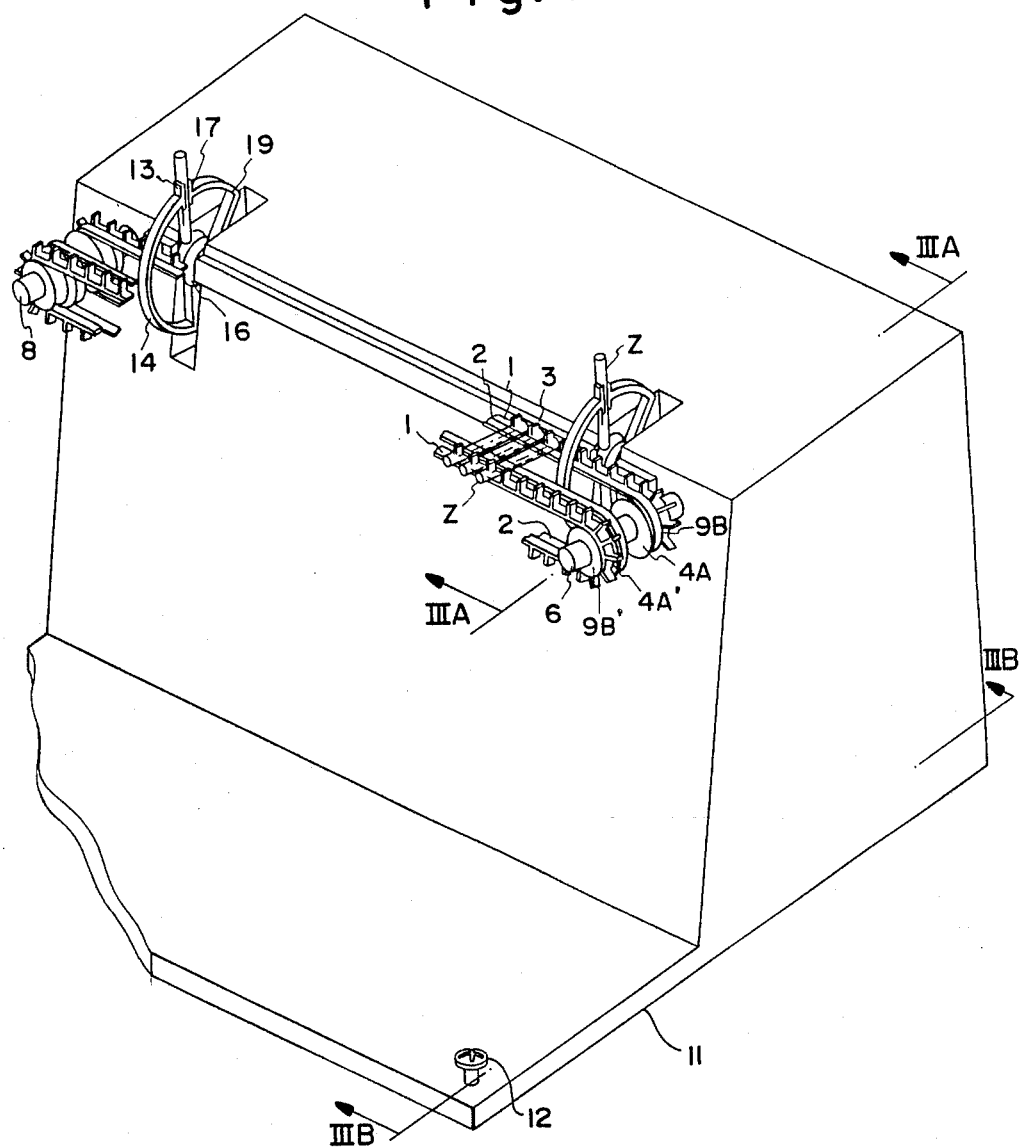
FIG. 1 is a perspective view illustrating a typical chemical reaction apparatus embodying the present invention.

Now, the functions fulfilled by the individual technical means which make up the chemical reaction apparatus of the present invention will be described below.

The inventor has ascertained that when reaction containers are placed on a travelling belt and stoppers like the teeth of a comb are disposed so as to prevent the reaction containers from being carried away by the belt in motion, the reaction containers are rotated about their own axes at a peripheral speed equalling the speed of the travel of the belt without slipping off the belt when in motion. Even in such a simple setup as described above, the reaction containers are rotated without producing the slightest slip and this setup functions effectively without the use of any complicated mechanism such as a belt used in a previous invention (type B) which drapes over the reaction containers and advances in a direction opposite the direction of travel of the belt provided for carrying the reaction containers. The certainty of the rotation of the reaction containers in this setup has been confirmed by visually counting the number of revolutions of the reaction containers with the aid of marks placed one each on the reaction containers. The results of this test are shown in Table 1.

TABLE 1

Relationship between the travelling speed of the belt and the number of revolutions and diameters of the reaction containers
Travelling speed of belt - 1068 mm/min

| Diameter of reaction container (mm) (A) | Reaction container No. | Number of revolutions in 10 minutes (found) (B) | $\frac{(A) \times \pi \times (B)}{10}$ (mm) |
|---|---|---|---|
| 9.9 | 1 | 344 | 1070 |
|  | 2 | 343 | 1067 |
|  | 3 | 343 | 1067 |
|  | 4 | 344 | 1070 |
|  | 5 | 343 | 1067 |
| 10.0 | 1 | 340 | 1068 |
|  | 2 | 340 | 1068 |
|  | 3 | 340 | 1068 |
|  | 4 | 340 | 1068 |
|  | 5 | 339 | 1065 |
| 10.1 | 1 | 337 | 1069 |
|  | 2 | 337 | 1069 |
|  | 3 | 337 | 1069 |
|  | 4 | 337 | 1069 |
|  | 5 | 337 | 1069 |
| 10.2 | 1 | 333 | 1067 |
|  | 2 | 334 | 1070 |
|  | 3 | 334 | 1070 |
|  | 4 | 334 | 1070 |

TABLE 1-continued

Relationship between the travelling speed of the belt and the number of revolutions and diameters of the reaction containers
Travelling speed of belt - 1068 mm/min

| Diameter of reaction container (mm) (A) | Reaction container No. | Number of revolutions in 10 minutes (found) (B) | $\frac{(A) \times \pi \times (B)}{10}$ (mm) |
|---|---|---|---|
|  | 5 | 333 | 1067 |

As shown above, the number of revolutions of the reaction containers is inversely proportional to their diameters. Furthermore, when the diameter of a reaction container (A) is multiplied by $\pi$ and by the number of revolutions and divided by 10, it will be equal to or very close to the distance the belt covers per minute.

The number of revolutions slightly varies among the reaction containers as shown in Table 1. It has been found that this can be ascribed to the fact that the diameters of the reaction containers slightly vary. In other words, this slight variance in the number of revolutions is not the result of the reaction containers slipping from the belt. When desired, the numbers can be made uniform by utilizing individual reaction containers of exactly the same diameters. Superficially, the fact that the reaction containers are rotated without slipping from the belt when in motion may seem to be a matter of everyday observation. However, the adoption of this principle has led to notable simplification of the apparatus. It has enabled mechanisms such as those for setting upright a reaction container to be incorporated in the apparatus at a desired position, so that such steps as introduction of specimens in reaction containers, rinsing of used reaction containers, and sampling of reaction mixtures, which had to be conventionally carried out while the reaction containers were held in the inclined state, can be carried out while the reaction containers are set upright. When such steps are performed with the reaction containers set upright, one or more reaction containers can be set upright all at once by synchronously actuating raising mechanisms located at desired positions. Thus, nozzles and other devices intended to perform the aforementioned steps may be disposed at desired positions on a horizontal bar disposed parallel to the direction of travel of the belt and adapted to move vertically and, by the vertical movement of the bar, may be synchronously reciprocated in the vertical direction. During this vertical reciprocation, the nozzles and other devices are allowed to fulfil their own functions.

The chemical reaction apparatus of the present invention has a simpler rotational mechanism than any other conventional apparatus as described above. Thus it permits the incorporation of a simple mechanism to advance the reaction containers sequentially at a fixed pitch. Also, as it is designed without any means such as a belt to suppress the reaction containers onto the apparatus itself, it has enabled the containers to be set upright at locations selected at will for performance of various steps of the process by a simple mechanism adapted to raise a reaction container with an upward push exerted from below or an upward pull exerted from above.

Owing to the construction described above, the present invention can manifest the following prominent effects which none of the conventional techniques could.

1. A multiplicity of small reaction containers can be easily and efficiently rotated simultaneously about their axes as held in the inclined state. Since all the reaction containers are slowly rotated at a fixed speed as inclined at a fixed angle, the stirring of their contents will be neither accelerated nor decelerated. Therefore the chemical reaction is enabled to proceed very uniformly and smoothly. The effect of the inclined rotation method adopted in the present invention on immunoreaction, as compared with the stationary method, is shown below in Table 2 and Table 4, and its effect on the propagation of rhinovirus is shown in Table 3.

2. Since the chemical reaction apparatus is capable of conveying a multiplicity of reaction containers collectively while keeping them rotated in the inclined state, it permits certain chemical reactions to be continuously carried out.

3. All the steps of the process can be carried out with the reaction containers held in the inclined state. Where they are judged to be carried out more advantageously with the reaction containers held upright, devices adapted to set a reaction container upright can be disposed at freely selected positions in the apparatus. Rinsing of the reaction containers to be performed at the position indicated by "b" in FIG. 5, for example, can be accomplished more advantageously when the reaction containers are held in the upright state for the rinsing solution can be completely removed and the incident of the solution overflowing can be reduced.

4. When the chemical reaction apparatus of this invention is interlocked with such a measuring instrument as a photometer, it is enabled to monitor the progress of a reaction and evaluate the outcome of the reaction automatically.

5. When the chemical reaction apparatus is provided with an optical or electromagnetic reading device, it is enabled to read out the information written on the reaction containers, i.e. the information regarding the test item and the reactivity of the reagent. Thus, otherwise possible confusion of test items and troublesome display of input data on the individual reaction containers can be eliminated.

6. By the incorporation of the functions mentioned above, the chemical reaction apparatus constitutes itself a setup befitting the performance of such chemical reactions as immunochemical reaction and enzyme reaction. Owing further to the automation of the operations involved, a number of dissimilar reactions can be continuously carried out quickly and accurately.

DESCRIPTION OF THE PREFERRED EMBODIMENT

Now, a typical chemical reaction apparatus embodying the present invention will be described below. This embodiment is just one example of the present invention, and therefore allows for various alterations of design.

First, the apparatus will be described with reference to the accompanying drawings.

Figure 2:
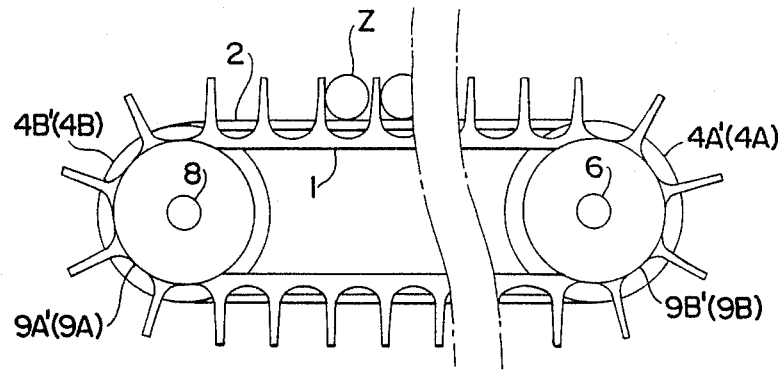
FIG. 2(A) is a front view of a belt driving mechanism for the apparatus of FIG. 1.
FIG. 2(B) is a top view of the belt driving mechanism for the apparatus of FIG. 1.
Figure 2:
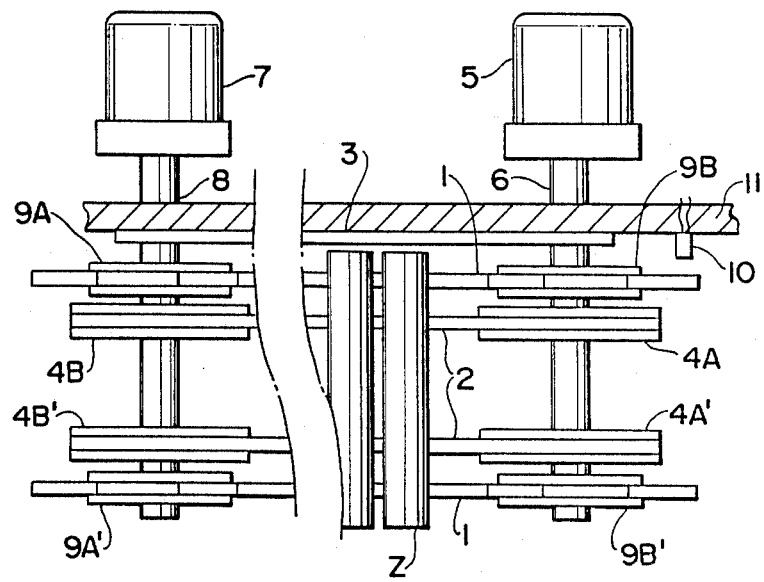

FIG. 1 portrays the chemical reaction apparatus in its entirety and FIG. 2(A) and FIG. 2(B) are explanatory diagrams illustrating the drive mechanism for the belt of the apparatus.

Reaction containers Z are supported in place by a set of two toothed retaining belts 1, a set of two travelling belts 2, and a base 3 adapted to prevent the reaction containers Z from slipping down along the angle of inclination. These reaction containers Z are rotated about their axes by the belts 2 which are advanced by the rotation of wheels 4A, 4A' fixed on a shaft 6 connected to a motor 5 which is fitted with a speed reducer. Wheels 9A, 9A' which are fixed on a shaft 8 connected to a motor 7 fitted with a speed reducer normally remain at rest to keep the reaction containers Z at their fixed positions. When the reaction containers Z are to be advanced at a fixed pitch, the motor 7 is set to forward the belts 1 and move the reaction containers Z by one pitch to their next positions. The distance over which the belts 1 are advanced at a pitch is fixed because the motor 7 is controlled and stopped when a detector such as photosensor 10 detects the positions of the teeth of a toothed retaining belt. Since wheels 4B, 4B' are not fixed on the shaft 8, they are rotated by the motion of the belts 2 produced in consequence of the rotation of the wheels 4A, 4A'. Since wheels 9B, 9B' are not fixed on the shaft 6, they are rotated by the motion of the belts 1 produced in consequence of the rotation of the wheels 9A, 9A'.

The mechanism described above is intended to cause a multiplicity of cylindrical reaction containers of the same size which are juxtaposed with their mouths up and their axes falling in a plane inclined at a fixed angle from the horizontal plane, rotated about their axes at a fixed rotational speed while retained in positions at an angle of inclination, so as to allow the required chemical reaction to proceed within. To ensure economization of reagents and specimens and enhancement of reaction efficiency, the angle of inclination of the reaction containers so held in place by the aforementioned mechanism may fall somewhere in the range of 0 to 45 degrees from horizontal, at which the reaction containers Z will not spill their contents. Generally, satisfactory results are obtained by selecting the angle in the range of 5 to 20 degrees (Table 4). The rotational speed of the reaction containers Z is desired to fall in the range 10 to 150 rpm. If the rotational speed is lower than 10 rpm, the stirring of the reaction mixtures in the reaction containers does not occur effectively. Conversely if it is higher than 150 rpm, the stirring does not occur efficiently because high molecular substances are inactivated by the mechanical impact or the liquids are rotated in conjunction with the reaction containers Z instead of flowing down the walls of the containers (Table 4).

The endless travelling belts 2 are so constructed that they will be continuously advanced at an equal speed by a drive device in one horizontal direction perpendicular to the axes of the reaction containers Z which supporting thereon the reaction containers Z. They are only required to remain in contact with the lower sides of the reaction containers Z and to rotate the reaction containers Z about their axes by virtue of the resultant friction. These belts 2 may be made of a material having a high coefficient of friction, such as polyurethane or chloroprene. The speed of the belts 2 can be freely adjusted by means of a motor fitted with a speed reducer and a pulley. In this case, the travelling speed of the belts 2 can be stabilized further by adopting timing belts as the belts 2 and timing pulleys specifically adapted for such belts as the pulleys.

The other endless retaining belts 1 which are disposed parallel and not contiguously to the aforementioned travelling belts, provided thereon with a multiplicity of teeth projecting up at fixed, spaced intervals slightly greater than the diameter of the reaction containers and adapted to retain the reaction containers at fixed relative positions, are only required to comprise belt webs made of such material as polyurethane or chloroprene and teeth planted on the belt webs at fixed, spaced intervals sufficient to admit the reaction containers Z therein and allow them to rotate freely therein. The teeth may be made of such material as "TEFLON" (tetrafluoroethylene), or polypropylene. To avoid obstructing the rotation of the reaction containers Z, the retaining belts are disposed at a position slightly lower than the travelling belts 2. It is desirable for the material of the teeth to have a friction coefficient lower than the friction coefficient of the travelling belts 2. The number of teeth can be selected so as to provide convenience of operation, the number preferably falls in the range of 20 to 200. In this case, the chemical reaction apparatus becomes a simpler and more reliable mechanism by adopting, as a retaining system, those timing belts which have teeth planted along the outer boundaries thereof.

The base 3 serving to support the bottoms of the reaction containers Z fulfils its function sufficiently by keeping the reaction containers Z from slipping down. It may be made of a metallic or a plastic material, having a low coefficient of friction. The drive device adapted to advance intermittently the retaining belts 1 at fixed intervals is installed for the purpose of feeding the reaction containers at a fixed pitch. The two retaining belts 1 are disposed one each along the mouth and the bottom of the reaction containers Z. By being synchronously moved, these retaining belts 1 enable the reaction containers Z placed thereon to be moved at a fixed pitch in a juxtaposed state. The time intervals with which the reaction containers Z are automatically advanced at a fixed pitch can be freely selected.

Figure 3A:
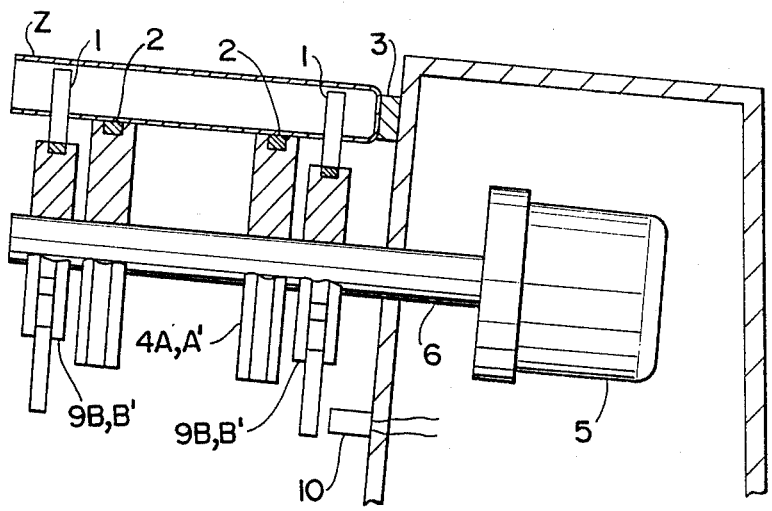
FIGS. 3(A) and 3(B) are cross sections respectively taken along the lines IIIA—IIIA and IIIB—IIIB of FIG. 1.
Figure 3B:
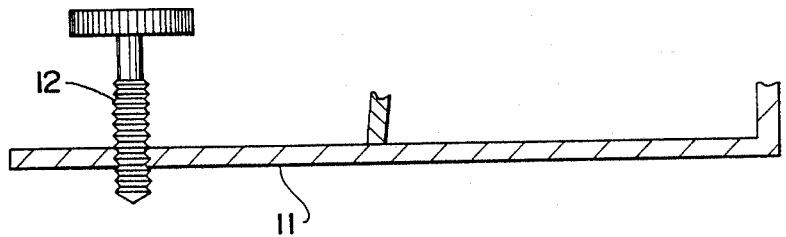

FIGS. 3(A) and 3(B) are cross sections respectively taken along the lines IIIA—IIIA and IIIB—IIIB of FIG. 1.

The reaction containers Z are supported in place by the set of two toothed retaining belts 1, the set of two travelling belts, and the base 3 disposed so as to keep the reaction containers Z from slipping down. They are rotated by the travelling belts which are driven by the rotation of the wheels 4A, 4A' fixed to the shaft 6 connected to the motor 5 fitted with the speed reducer. The angle of inclination of the reaction containers Z is adjusted by turning a screw 12 fitted to a bottom portion of the frame 11 at the end portion of the side where the reaction containers Z are disposed.

FIGS. 4(I)–4(V) are explanatory diagrams illustrating a mechanism for setting upright the inclined reaction containers at stated positions in the apparatus.

FIG. 4(I) represents an embodiment using two travelling belts. A holder 13 is joined through an arm 14 integrally to a rotary plate 16 which is connected to a shaft 15. The rotary plate 16 is disc-shaped. To this rotary plate 16 is fixed one end of the arm 14, which is in the shape of a semi-circular arc. The other end of the arm 14 is provided with the holder 13. The claw 22 is provided on the circumferential face of rotary plate 16 at a place in line with the holder 13 and the shaft 15. A holder 17 is integrally joined to one end of a substantially Z-shaped arm 19 which includes a metal member 18 having at aperture therein through which shaft 15 extends. The metal member 18 is adapted to be freely rotated about the shaft 15. The end of arm 19 not joined to holder 17 is pulled by a spring 20 (the other end of which is connected to a fixed point on the apparatus) and retained at a fixed position shown in FIG. 4(I) by a stopper 21.

As a consequence of the rotation of the shaft 15 (by conventional means not shown) in the clockwise direction, the holder 13 rises in conjunction with a claw 22 through the medium of the rotary plate 16 and the arm 14 to push up the reaction container Z. The holder 13, during the rise, cooperates with the holder 17 and the claw 22 to pinch the reaction container Z and then continues to rise. When the reaction container Z is brought to the upright position as shown in FIG. 4(II), the shaft 15 discontinues its rotation (as controlled by conventional means not shown). Then, when the shaft 15 is rotated in the counterclockwise direction, the reaction container Z is returned to its original state as shown in FIG. 4(I). FIG. 4(III) and FIG. 4(IV) represent an embodiment using one travelling belt 2. In the mechanism illustrated, the holder 13 pushes up the upper end of the reaction container Z and the holder 17 and the claw 22 pinch the reaction container Z and set it upright. FIG. 4(V) illustrates the reaction container Z as pinched between the holders 13, 17.

FIG. 5 is a front view of the apparatus laid so as to correspond to the process of the immunoreaction. Raising devices constructed and arranged in accordance with FIGS. 4(I)–4(V), described hereinafter as located at positions "a", "b", "c", have been omitted from FIG. 5 for simplicity.

A reaction container feeder 23 which accommodates therein reaction containers Z containing an enzyme labeled antibody therein and having the antibody immobilized to the inner walls thereof feeds out the reaction containers Z sequentially. When the first reaction container Z reaches the position "a", the associated raising device is actuated to set the first reaction container Z upright. The specimen injector which has drawn the specimen from the specimen turntable injects a fixed amount of the specimen together with a buffer solution into the reaction container Z. Then, the raising device is returned to its normal position and, thereafter, the reaction container Z is rotated about its axis on the belts 2 and advanced toward the right. As the reaction container Z is advanced the immunoreaction occurs inside the reaction container Z. By the retaining belts 1, the subsequent reaction containers Z are successively moved at fixed time intervals toward the right, each undergoing the same steps of raising and injection. When the first reaction container Z reaches the position "b", the raising device located at the position "b" is actuated to set the first reaction container upright once again. The rinsing device empties the reaction container Z of the spent reaction mixture by suction. Then, it injects the rinsing liquid to cleanse the interior. The steps of injecting and sucking out the rinsing liquid are alternately repeated until the reaction container Z is thoroughly cleaned. Subsequently, the substrate solution for enzyme is injected by the dispensing device into the reaction container Z, and the raising device at the position "b" is returned to its normal position. The reaction container Z is then moved to the position "c". During this period, the enzyme reaction occurs inside the reaction container Z. At the position "c", the associated raising device is actuated to set the reaction container Z upright, so as to make the next process easy. The next process is carried out to determine the result by conveying and inserting the reaction container manually or mechanically into the spectrophotometer. The raising device at the position "c" returns to the normal position after the reaction container is removed. The positions "b" and "c" are determined by reaction time and the pitch. The specimen injector, specimen turntable, rinsing device, dispensing device and spectrophotometer are conventional features well known to those skilled in the art, and are therefore shown only symbolically in FIG. 5.

The injection device for introducing the reagent into the reaction container is preferred to possess precision equivalent to the precision expected of fine analysis such as radioimmunoassay and to be capable of exactly separating a fixed amount of reagent exactly and introducing the reagent so separated into the reaction container. Although the injection device may, as described above, introduce reagent into the reaction container with the reaction container in an upright state, the injection device may also introduce reagent into the reaction container with the reaction container in an inclined state. Where it is preferred that the specimen or the reagent be diluted, the so-called diluting dispenser can be used which is capable of effecting the required dilution with a proper amount of diluent. For general use, any of the dispensing devices can be adopted in its unmodified form. Optionally, two or more such dispensing devices may be used at separated positions.

It is desirable that the rinsing device for cleaning the inside of the reaction container comprises a combination of two cylinder type dispensers, one for removal by suction and the other for introduction by injection, or a combination of a dispenser using a water pump for introduction and a timer and a solenoid valve for control of flow volume with a device for effecting removal by suction under a vacuum.

When the reaction containers are tightly sealed before use, it is preferred that the chemical reaction apparatus incorporate an opening device, for removing the seals from the reaction containers with the reaction containers in either an upright state or an inclined state, at a position between feeder 23 and position "a".

As the measuring device for testing the reaction mixture in the reaction container for optical density, a spectrophotometer or a fluorophotometer can be utilized. The device so adopted may be of the flow type or discrete type.

Test Example

Tests were carried out with chemical reaction apparatuses embodying the present invention. The results are shown in Table 2 and Table 3.

Table 2 shows the effect brought about by the use of the inclined rotation technique in the enzyme immunoassay for carcinoembryonic antigen (CEA).

TABLE 2

| Effect of inclined rotation technique upon reaction | |
|---|---|
| Condition | Intensity of coloration |
| Standing at rest in upright state | 100 |
| Angle of inclination 10 degrees and rotational speed 30 r.p.m. | 313 |
| Angle of inclination 10 degrees and rotational speed 240 r.p.m. | 159 |

Test tubes with inner diameters of 12 mm, each containing a polystyrene bead 6 mm in diameter having an anti-CEA antibody immobilized thereon, 0.1 ml of specimen containing CEA of concentration of 10 ng/ml, and 0.4 ml of an enzyme labelled anti-CEA antibody solution, were left to undergo immunoreaction at 25° C. for 20 minutes at an angle of 90 degrees (upright) and a rotation speed of 0 r.p.m. (standing at rest) and an an angle of 10 degrees and rotation speeds of 30 and 240 r.p.m. To check the amount of the enzyme labelled antibody bound through CEA to the immobilized antibody, the enzyme labelled antibody which had failed to be bound was removed by rinsing. Then the residue, with hydrogen peroxide as the substrate for the enzyme and ortho-phenylenediamine as a chromogen added thereto, was subjected to enzyme reaction under the same conditions for 10 minutes. Since peroxidase was used as the enzyme, it activated hydrogen peroxide and caused coloration of the ortho-phenylenediamine. In the table, the numerical values stated under "intensity of coloration" represent relative magnitudes, setting the intensity found when the reaction container was set upright and still as 100. It can be noted that 30 r.p.m. and 240 r.p.m. rotations enhanced the reaction 3.1 and 1.6 times respectively compared with the situation when the reaction containers were set upright without any rotation.

Table 3 shows the effect of the inclined rotation on the propagation of rhinovirus.

TABLE 3

| Potency of rhinovirus type 3 in 1 ml of supernatant | |
|---|---|
| Method of culture | Virus potency ($TCID_{50}$) |
| Rotary culture | $10^{8.3}$ |
| Stationary culture | $10^{7.1}$ |

In a plastic test tube (16×125 mm), 3 ml of Eagle Basal medium, containing 10% bovine fetal serum and having Ohio Hela cells suspended therein at a concentration of $1 \times 10^6$ cells per ml, was subjected to rotary culture at 37° C. for three days on an apparatus having an inclination of 10 degrees and a rotation speed of 30 r.p.m. From the resultant culture broth, the supernatant was removed and discarded. The residue of the culture broth, with 0.5 ml of Eagle Basal medium containing rhinovirus type 3 suspended at a concentration of $10^{5.0}$ of 50% tissue culture infectious dose ($TCID_{50}$) added thereto, was subjected to rotary culture for one hour. The residue, with 2.5 ml of the same medium added thereto, was similarly subjected to rotary culture for three days. The supernatant consequently formed was gathered and tested for virus potency, $TCID_{50}$, by the method proposed by H. L. Torney et al., Antimicrobial Agents and Chemotherapy 22, 635–638 (1982). In a plastic Roux flask (25 cm$^2$), Ohio Hela cells inoculated at a concentration of $3 \times 10^6$ cells per ml were left undergoing stationary culture for three days. The resultant culture broth, with the medium substituted with 0.5 ml of a medium containing rhinovirus type 3 suspended at a concentration of $10^{5.0}$ $TCID_{50}$, was subjected to stationary culture for one hour. The culture broth, with 9.5 ml of the same medium further added thereto, was left undergoing stationary culture for three days. The supernatant consequently formed was gathered and tested for virus potency, $TCID_{50}$, by following the procedure described above. As indicated in the table, the propagation of virus by rotary culture was more than 10 times as effective as that by stationary culture.

Test Example

Table 4 shows the effects of the angle of inclination and rotation speed on reaction.

TABLE 4

Effects of the angle of inclination and rotation speed on reaction (indicated in relative magnitudes of intensity of coloration, setting the intensity obtained when the reaction containers were inclined 90 degrees and no rotation was added as 100)

| Angle of inclination (degrees) | Rotation speed (r.p.m.) | | | | | |
|---|---|---|---|---|---|---|
| | 0 | 5 | 30 | 60 | 120 | 240 |
| 90 | 100 | 106 | 123 | 159 | 180 | 134 |
| 60 | — | 166 | 206 | 245 | 270 | 174 |
| 30 | — | 294 | 320 | 357 | 384 | 238 |
| 10 | — | 296 | 399 | 403 | 329 | 214 |

The table given above compares the effect of inclined rotation on the enzyme immunoassay for α-fetoprotein (AFP). Cylindrical reaction containers having an inner diameter of 9 mm, each containing anti-AFP antibody immobilized on the inner surface near the bottom, 0.05 ml of specimen containing AFP at a concentration of 20 ng/ml and 0.20 ml of an enzyme labelled anti-AFP antibody solution, were set at varying angles of inclination, 90 degrees (upright state), 60 degrees, 30 degrees, and 10 degrees and rotated at varying speeds 0 (absence of rotation), 5, 30, 60, 120, and 240 r.p.m. to effect immunochemical reaction at 25° C. for 20 minutes. To check the amount of the enzyme labelled antibody bound through AFP to the immobilized antibody, the enzyme labelled antibody which had failed to be bound was removed by rinsing. The residue, with hydrogen peroxide as the substrate for the enzyme and ortho-phenylenediamine as a chromogen added thereto, was left undergo enzyme reaction for 10 minutes under same conditions. Since peroxidase was used as the enzyme, it activated the hydrogen peroxide and caused coloration of ortho-phenylenediamine. The numerical values given in the table represent relative magnitudes, setting the intensity of coloration obtained when the reaction containers were set upright and still as 100. In all the reaction conditions used herein, the coloration occurred with the highest intensity when the containers were inclined 10 to 30 degrees and rotated at speeds ranging from 30 to 120 r.p.m. These specific conditions enhanced the reaction about 4 times as compared to the situation when the reaction containers were set upright and still. It was also found that excessive rotation impeded rather than enhanced reaction. This disadvantage of the excessive rotation may be logically explained by a postulate that, during the immunoreaction, high molecular substances are inactivated by mechanical impact and the efficiency of this reaction is consequently degraded.

What is claimed is:

1. A chemical reaction apparatus comprising:
 a plurality of cylindrical reaction containers;
 at least one endless travelling belt constructed and arranged for supporting thereon said plurality of cylindrical reaction containers arranged in parallel;
 driving means for advancing said at least one travelling belt at a constant speed in one horizontal direction;
 separate endless retaining belts disposed on each side of said at least one travelling belt, said retaining belts being disposed parallel to and not contiguously to said at least one travelling belt, each retaining belt being provided thereon with a multiplicity of teeth projecting up at fixed, spaced intervals slightly greater than the diameter of said reaction containers, and adapted to retain said reaction containers at fixed relative positions, portions of said retaining belt teeth being positioned lower than the surface of the travelling belt;
 a base on a frame of the apparatus adjacent said at least one endless travelling belt and said endless retaining belts constructed and arranged for supporting bottoms of said reaction containers;
 drive means for advancing said retaining belts intermittently over fixed intervals of space; and
 means for maintaining said cylindrical reaction containers on said at least one travelling belt at an angle inclined with respect to a horizontal plane;
 said base and retaining belts cooperating with one another to maintain the plurality of cylindrical reaction containers in juxtaposed position relative to one another with respective tops of the containers positioned above corresponding container bottoms so that a central axis of each of the containers is on a plane inclined at said angle relative to a horizontal plane; and said travelling belt driving means and said retaining belt drive means cooperating with one another and with said travelling and retaining belts to rotate each container about its respective central axis and allow a required chemical reaction to proceed therein.

2. A chemical reaction apparatus according to claim 1, which further comprises an injection device for introducing reagent into said reaction containers with said reaction containers at said angle of inclination.

3. A chemical reaction apparatus according to claim 1, which further comprises a rinsing device constructed and arranged to rinse said reaction containers.

4. A chemical reaction apparatus according to claim 2, which further comprises a rinsing device constructed and arranged to rinse said reaction containers.

5. A chemical reaction apparatus according to claim 1, which further comprises an oopening device for removing seals from said reaction containers, with said reaction containers at said angle of inclination, when said reaction containers are tightly sealed.

6. A chemical reaction apparatus according to claim 2, which further comprises an opening device for removing seals from said reaction containers, with said reaction containers at said angle of inclination, when said reaction containers are tightly sealed.

7. A chemical reaction apparatus according to claim 3, which further comprises an opening device for removing seals from said reaction containers, with said reaction containers at said angle of inclination, when said reaction containers ae tightly sealed.

8. A chemical reaction apparatus according to claim 4, which further comprises an opening device for removing seals from said reaction containers, with said reaction containers at said angle of inclination, when said reaction containers are tightly sealed.

9. A chemical reaction apparatus according to claim 1, which further comprises a sampling device for drawing samples of reaction mixtures from said reaction containers with said reaction containers at said angle of inclination.

10. A chemical reaction apparatus according to claim 2, which further comprises a sampling device for drawing samples of reaction mixtures from said reaction containers with said reaction containers at said angle of inclination.

11. A chemical reaction apparatus according to claim 3, which further comprises a sampling device for drawing samples of reaction mixtures from said reaction containers with said reaction containers at said angle of inclination.

12. A chemical reaction apparatus according to claim 4, which further comprises a sampling device for drawing samples of reaction mixtures from said reaction containers with said reaction containers at said angle of inclination.

13. A chemical reaction apparatus according to claim 5, which further comprises a sampling device for drawing samples of reaction mixtures from said reaction containers with said reaction containers at said angle of inclination.

14. A chemical reaction apparatus according to claim 6, which further comprises a sampling device for drawing samples of reaction mixtures from said reaction containers with said reaction containers at said angle of inclination.

15. A chemical reaction apparatus according to claim 7, which further comprises a sampling device for drawing samples of reaction mixtures from said reaction containers with said reaction containers at said angle of inclination.

16. A chemical reaction apparatus according to claim 8, which further comprises a sampling device for drawing samples of reaction mixtures from said reaction containers with said reaction containers at said angle of inclination.

17. A chemical reaction apparatus according to claim 1, which further comprises a measuring device for testing reaction mixtures in said reaction containers for optical density.

18. A chemical reaction apparatus according to claim 2, which further comprises a measuring device for testing reaction mixtures in said reaction containers for optical density.

19. A chemical reaction apparatus according to claim 3, which further comprises a measuring device for testing reaction mixtures in said reaction containers for optical density.

20. A chemical reaction apparatus according to claim 4, which further comprises a measuring device for testing reaction mixtures in said reaction containers for optical density.

21. A chemical reaction apparatus according to claim 5, which further comprises a measuring device for testing reaction mixtures in said reaction containers for optical density.

22. A chemical reaction apparatus according to claim 6, which further comprises a measuring device for testing reaction mixtures in said reaction containers for optical density.

23. A chemical reaction apparatus according to claim 7, which further comprises a measuring device for testing reaction mixtures in said reaction containers for optical density.

24. A chemical reaction apparatus according to claim 8, which further comprises a measuring device for testing reaction mixtures in said reaction containers for optical density.

25. A chemical reaction apparatus according to claim 9, which further comprises a measuring device for testing the reaction mixtures in said reaction containers for optical density.

26. A chemical reaction apparatus according to claim 10, which further comprises a measuring device for testing the reaction mixtures in said reaction containers for optical density.

27. A chemical reaction apparatus according to claim 11, which further comprises a measuring device for testing the reaction mixtures in said reaction containers for optical density.

28. A chemical reaction apparatus according to claim 12, which further comprises a measuring device for testing the reaction mixture in said reaction containers for optical density.

29. A chemical reaction apparatus according to claim 13, which further comprises a measuring device for testing the reaction mixtures in said reaction containers for optical density.

30. A chemical reaction apparatus according to claim 14, which further comprises a measuring device for testing the reaction mixtures in said reaction containers for optical density.

31. A chemical reaction apparatus according to claim 15, which further comprises a measuring device for testing the reaction mixtures in said reaction containers for optical density.

32. A chemical reaction apparatus according to claim 16, which further comprises a measuring device for testing the reaction mixtures in said reaction containers for optical density.

33. A chemical reaction apparatus comprising:
a plurality of cylindrical reaction containers;
at least one endless travelling belt constructed and arranged for supporting thereon said plurality of cylindrical reaction containers arranged in parallel;
driving means for advancing said at least one travelling belt at a constant speed in one horizontal direction;
separate endless retaining belts disposed on each side of said at least one travelling belt, said retaining belts being disposed parallel to and not contiguously to said at least one travelling belt, each retaining belt being provided thereon with a multiplicity of teeth projecting up at fixed, spaced intervals slightly greater than the diameter of said reaction containers, and adapted to retain said reaction containers at fixed relative positions, portions of said retaining belt teeth being positioned lower than the surface of the travelling belt;
a base on a frame of the apparatus adjacent said at least one endless travelling belt and said endless retaining belts constructed and arranged for supporting bottoms of said reaction containers;
drive means for advancing said retaining belts intermittently over fixed intervals of space;
means for maintaining said cylindrical reaction containers on said at least one travelling belt at an angle inclined with respect to a horizontal plane; and
at least one raising device located along said travelling and retaining belts, said at least one raising device having means for supporting a lower side and an upper side of each container, said raising device supporting means having members that can engage and disengage the sides of each container so that the container may be moved from an inclined position when supported by said travelling and retaining belts, to a vertical upright position for dispensing, and back to the inclined position for conveyance by said travelling and retaining belts;
said base and retaining belts cooperating with one another to maintain the plurality of cylindrical reaction containers in juxtaposed position relative to one another with respective tops of the containers positioned above corresponding container bottoms so that a central axis of each of the containers is on a plane inclined at said angle relative to a horizontal plane; and said travelling belt driving means and said retaining belt drive means cooperating with one another and with said travelling and retaining belts to rotate each container about its respective central axis and allow a required chemical reaction to proceed therein.

34. A chemical reaction apparatus according to claim 33, which further comprises an injection device for introducing reagent into said reaction containers with said reaction containers in an upright state.

35. A chemical reaction apparatus according to claim 33, which further comprises a rinsing device constructed and arranged to rinse said reaction containers.

36. A chemical reaction apparatus according to claim 34, which further comprises a rinsing device constructed and arranged to rinse said reaction containers.

37. A chemical reaction apparatus according to claim 33, which further comprises an opening device for removing seals from said reaction containers, with said reaction containers in an upright state, when said reaction containers are tightly sealed.

38. A chemical reaction apparatus according to claim 34, which further comprises an opening device for removing seals from said reaction container containers, with said reaction containers in an upright state when said reaction containers are tightly sealed.

39. A chemical reaction apparatus according to claim 35, which further comprises an opening device for removing seals from said reaction containers, with said reaction containers in an upright state, when said reaction containers are tightly sealed.

40. A chemical reaction apparatus according to claim 36, which further comprises an opening device for removing seals from said reaction containers, with said reaction containers in an upright state, when said reaction containers are tightly sealed.

41. A chemical reaction apparatus according to claim 33, which further comprises a sampling device for drawing samples of reaction mixtures from said reaction containers with said reaction containers in an upright state.

42. A chemical reaction apparatus according to claim 34, which further comprises a sampling device for drawing samples of reaction mixtures from said reaction containers with said reaction containers in an upright state.

43. A chemical reaction apparatus according to claim 35, which further comprises a sampling device for drawing samples of reaction mixtures from said reaction containers with said reaction containers in an upright state.

44. A chemical reaction apparatus according to claim 36, which further comprises a sampling device for drawing samples of reaction mixtures from said reaction containers with said reaction containers in an upright state.

45. A chemical reaction apparatus according to claim 37, which further comprises a sampling device for drawing samples of reaction mixtures from said reaction containers with said reaction containers in an upright state.

46. A chemical reaction apparatus according to claim 38, which further comprises a sampling device for drawing samples of reaction mixtures from said reaction containers with said reaction containers in an upright state.

47. A chemical reaction apparatus according to claim 39, which further comprises a sampling device for drawing samples of reaction mixtures from said reaction containers with said reaction containers in an upright state.

48. A chemical reaction apparatus according to claim 40, which further comprises a sampling device for drawing samples of reaction mixtures from said reaction containers with said reaction containers in an upright state.

49. A chemical reaction apparatus according to claim 33, which further comprises a measuring device for testing reaction mixtures in said reaction containers for optical density.

50. A chemical reaction apparatus according to claim 34, which further comprises a measuring device for testing reaction mixtures in said reaction containers for optical density.

51. A chemical reaction apparatus according to claim 35, which further comprises a measuring device for testing reaction mixtures in said reaction containers for optical density.

52. A chemical reaction apparatus according to claim 36, which further comprises a measuring device for testing reaction mixtures in said reaction containers for optical density.

53. A chemical reaction apparatus according to claim 37, which further comprises a measuring device for testing reaction mixtures in said reaction containers for optical density.

54. A chemical reaction apparatus according to claim 38, which further comprises a measuring device for testing reaction mixtures in said reaction containers for optical density.

55. A chemical reaction apparatus according to claim 39, which further comprises a measuring device for testing reaction mixtures for said reaction containers for optical density.

56. A chemical reaction apparatus according to claim 40, which further comprises a measuring device for testing reaction mixtures in said reaction containers for optical density.

57. A chemical reaction apparatus according to claim 41, which further comprises a measuring device for testing the reaction mixtures in said reaction containers for optical density.

58. A chemical reaction apparatus according to claim 42, which further comprises a measuring device for testing the reaction mixtures in said reaction containers for optical density.

59. A chemical reaction apparatus according to claim 43, which further comprises a measuring device for testing the reaction mixtures in said reaction containers for optical density.

60. A chemical reaction apparatus according to claim 44, which further comprises a measuring device for testing the reaction mixtures in said reaction containers for optical density.

61. A chemical reaction apparatus according to claim 45, which further comprises a measuring device for testing the reaction mixtures in said reaction containers for optical density.

62. A chemical reaction apparatus according to claim 46, which further comprises a measuring device for testing the reaction mixtures in said reaction containers for optical density.

63. A chemical reaction apparatus according to claim 47, which further comprises a measuring device for testing the reaction mixtures in said reaction containers for optical density.

64. A chemical reaction apparatus according to claim 48, which further comprises a measuring device for testing the reaction mixtures in said reaction containers, for optical density.

* * * * *